United States Patent
Kuris et al.

(10) Patent No.: US 8,223,013 B2
(45) Date of Patent: Jul. 17, 2012

(54) METHOD AND MECHANISM FOR ASSISTED DIAGNOSIS AND MAINTENANCE OF HEALTH MONITORING SYSTEM

(75) Inventors: Benjamin Kuris, Cambridge, MA (US); Donald R. Denning, Jr., Boston, MA (US); Steven M. Ayer, Marblehead, MA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 633 days.

(21) Appl. No.: 11/960,955

(22) Filed: Dec. 20, 2007

(65) Prior Publication Data
US 2009/0015403 A1    Jan. 15, 2009

Related U.S. Application Data

(63) Continuation-in-part of application No. 11/646,599, filed on Dec. 28, 2006.

(51) Int. Cl.
*H03L 7/00* (2006.01)
*H04N 5/04* (2006.01)
*H04N 9/44* (2006.01)
(52) U.S. Cl. .................. 340/539.22; 340/511
(58) Field of Classification Search ........... 340/539.22, 340/870.01
See application file for complete search history.

(56) References Cited

U.S. PATENT DOCUMENTS

| | | | |
|---|---|---|---|
| 5,640,143 A * | 6/1997 | Myron et al. ............ 340/541 |
| 6,351,713 B1 | 2/2002 | Board et al. | |
| 7,142,123 B1 * | 11/2006 | Kates ..................... 340/602 |
| 7,399,277 B2 | 7/2008 | Saidara et al. | |
| 2002/0158775 A1 * | 10/2002 | Wallace ............... 340/870.07 |
| 2003/0128118 A1 * | 7/2003 | Leyden et al. ............ 340/568.2 |
| 2004/0130446 A1 * | 7/2004 | Chen et al. ............. 340/539.12 |
| 2005/0017873 A1 * | 1/2005 | Liu et al. .............. 340/870.01 |
| 2006/0028335 A1 * | 2/2006 | Glenn et al. ............ 340/531 |
| 2006/0062201 A1 * | 3/2006 | Funk et al. ............. 370/352 |
| 2006/0155818 A1 * | 7/2006 | Odenwald et al. .......... 709/208 |
| 2006/0190458 A1 | 8/2006 | Mishina et al. | |
| 2006/0242285 A1 | 10/2006 | Moriwaki | |
| 2007/0069892 A1 | 3/2007 | Paul et al. | |

FOREIGN PATENT DOCUMENTS

| KR | 20040031733 | 4/2004 |
| KR | 1020040031733 | 4/2004 |

OTHER PUBLICATIONS

International Preliminary Report on Patentability issued on Jul. 9, 2009 in International Application No. PCT/US2007/089055.
Chinese Office Action with English translation corresponding to International Application CN 200710305273.7, dated Aug. 27, 2010.

* cited by examiner

*Primary Examiner* — Benjamin C Lee
*Assistant Examiner* — Cal Eustaquio
(74) *Attorney, Agent, or Firm* — Pillsbury Winthrop Shaw Pittman LLP

(57) ABSTRACT

The invention relates to a system and method of a health monitoring network which automates detection of faulty or failed sensors using real-time fault checking on a dynamically registered sensor data stream. The monitoring system and sensor network can provide a one-touch system to notify users when a sensor requires attention, without prior knowledge of the operational characteristics, installation method or configuration of sensors in the network. The network uses a decision engine to assist in maintenance according to a profile based on individual preferences and capabilities.

26 Claims, 7 Drawing Sheets

Exemplary Psuedo-code for Decision Engine:

...
<IF> UserButton pressed
<THEN> *query* BatteryVoltage for all Sensors[n]
  <IF> Sensor[i] has CriticalBatteryLevel
  <THEN> *IndicateAttention* on Sensor[i]
    <ELSE> *Load* MaintenenceProfile
      <IF> Sensors match MaintenanceProfile
      <THEN> *SelectBestSensor* out of Sensors[m]
          *IndicateAttention* on Sensor[j]

Continuous Loop based on Sample Rate

METHOD AND MECHANISM FOR ASSISTED DIAGNOSIS AND MAINTENANCE OF HEALTH MONITORING SYSTEM

CROSS-REFERENCE TO RELATED APPLICATIONS

This application is a continuation-in-part of and claims the benefit under 35 U.S.C. 120 of co-pending U.S. application Ser. No. 11/646,599, filed on Dec. 28, 2006, the entire content of which is incorporated herein by reference.

FIELD OF THE INVENTION

The invention relates to a system and method for a health monitoring network which automates detection of faulty or failed sensors, assists in the maintenance of, based on customizable profiles preferences and capabilities.

BACKGROUND

Existing solutions are designed with limited run time to avoid the need for unsupervised system maintenance. Administration requires expertise and training in the system. Additionally, work on multi-sensor health monitoring systems focuses on communication methods, data analysis, and transducer efficacy. Practical issues in multi-sensor deployment, especially multi-sensor on-body deployments such as maintaining a multi-sensor system with zero-training and minimal inconvenience are virtually non-existent.

Common methods include some form of the BIST (built-in self test) on sensor nodes, and manual inspection of data during installation and after loss of data is detected. The execution or interpretation of results from these methods requires technical knowledge that most users lack. Finally, there are substantial periods of missing data when manual inspections are not regularly conducted.

DETAILED DESCRIPTION

The embodiments of the invention relates a system for maintaining a sensor network, the sensor network comprising at least one sensor; a base station adapted to receive data from the sensor network; at least one sensor being adapted to communicate data to the base station; a fault-detection system adapted to analyze data from the at least one sensor and determine an operating state of the at least one sensor, wherein the fault-detection system is located in the base station or on a remote computing resource; and a decision engine embedded in the base station or on the remote computing source, the decision engine being adapted to activate a sensor attention indicator based on an output from the fault-detection system indicative of an operating state of the at least one sensor. Preferably, the sensor network is adapted for health monitoring sensor network.

Yet other embodiments of the invention relate to a method for maintaining a sensor network, comprising providing the sensor network comprising at least one sensor; providing a base station adapted to receive data from the sensor network; the at least one sensor being adapted to communicate data to the base station; providing a fault-detection system adapted to analyze data from the at least one sensor and determine an operating state of the at least one sensor, wherein the fault-detection system is located in the base station or on a remote computing resource; and providing a decision engine embedded in the base station or on the remote computing source, the decision engine being adapted to activate a sensor attention indicator based on an output from the fault-detection system indicative of an operating state of the at least one sensor.

A "sensor network" is a network of autonomous devices deployed to collect data with some means to aggregate the data collected. A health monitoring sensor network is a sensor network where the goal is to collect data relevant to health issues including (a) wearable patient/user monitoring: psychological (ECG, heart rate etc.) or behavioral (movement, socialization, object use, etc.); (b) occupant monitoring from a fixed location in a building; and (c) environmental monitoring, for example, in changes in condition in the local environment (temperature, air quality, etc.).

Figure 1:
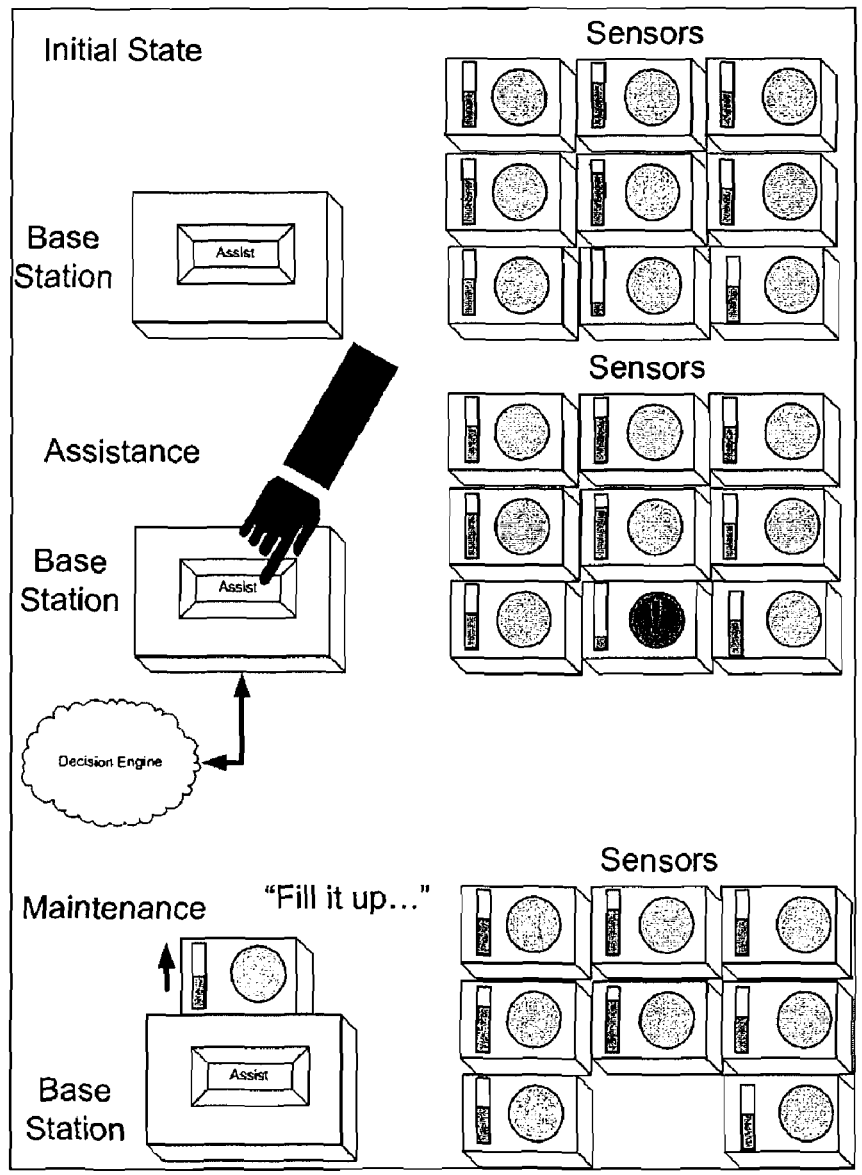
FIG. 1 illustrates an exemplary embodiment in accordance with the embodiments of the invention.

FIG. 1 shows the time-sequence of events of one embodiment for the system and demonstrates how a user could use the system with little training to perform a potentially complex sensor network maintenance procedure. The elements are a base station with a user button labeled, "Assist", and many sensors with indicators (initially inactive as shown by the grey circles) and a consumable component such as battery voltage represented as a fluid level.

From an initial point in time, the user then employs the invention for assistance in maintaining the sensor network. To do so the user presses the Assist button on the base-station. The base-station then uses the decision engine (in this case a remote resource as indicated by the cloud) to compute the correct assistance output. In this case, an indicator is activated on the sensor with the lowest consumable level (battery voltage). To complete maintenance, the user could place a sensor on the base-station where a consumable resource of the sensor (such battery charge) could be replenished.

Below the schematic of FIG. 1, a pseudo-code is provided to explain the operation of the decision engine for a useful scenario, namely, immediately indicating any sensor faults or in absence of a fault, selecting the best single sensor from a multitude of sensors for maintenance.

Figure 2:
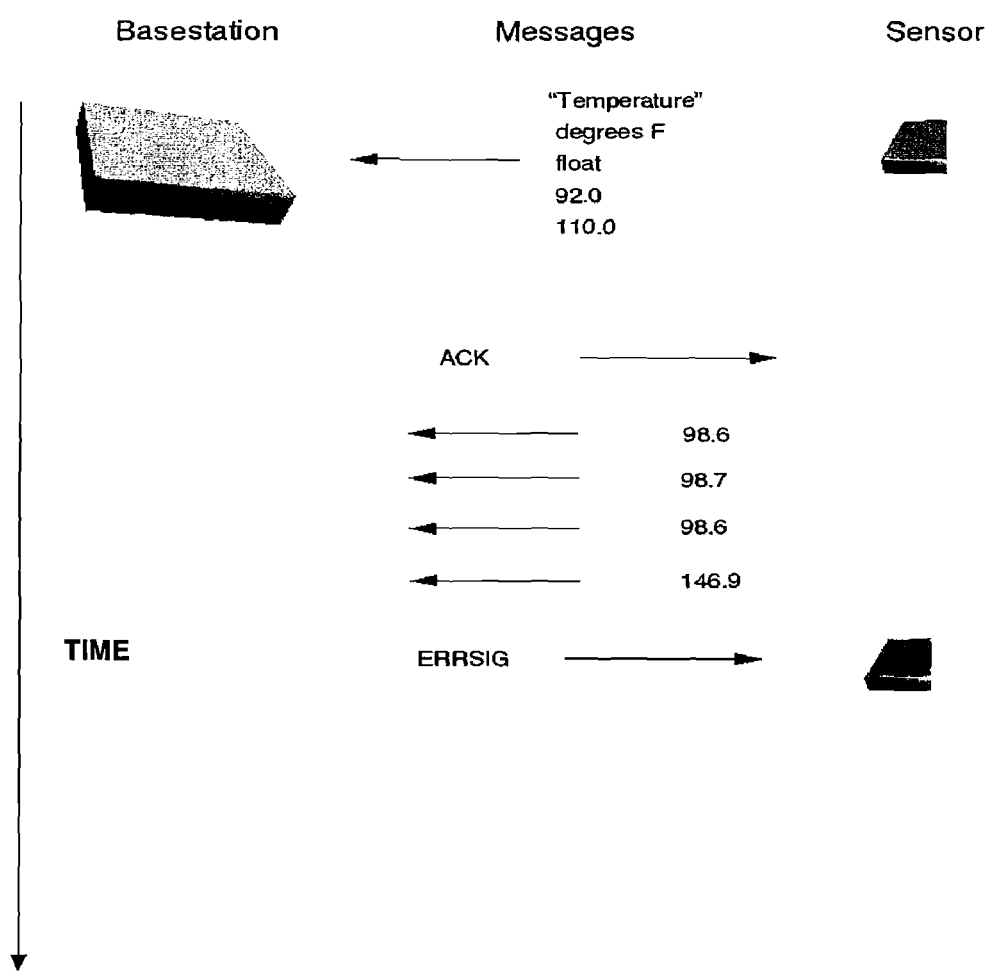
FIG. 2 illustrates an exemplary flow between the base state, messages and sensors in accordance with an embodiment of the invention.

FIG. 2 shows a time-sequence of data-checking aspects of the invention in operation. First the sensor sends a message to the base-station to register its data output. The message includes a valid output range—for simplicity, in this case, the decision engine could be rule-based and merely checks incoming data to ensure that it is within a range. The base-station could respond to the sensor with an acknowledgement message that signifies a successful sensor registration. A series of data values could then be transmitted. For example, the first three could be within range, while the next exceeds the upper bound on the range. The base-station responds with an error signal that actuates an alert on the sensor. The actuation could be indicated by a color change on the sensor node which may correspond to the color of an LED indicator.

Figure 3:
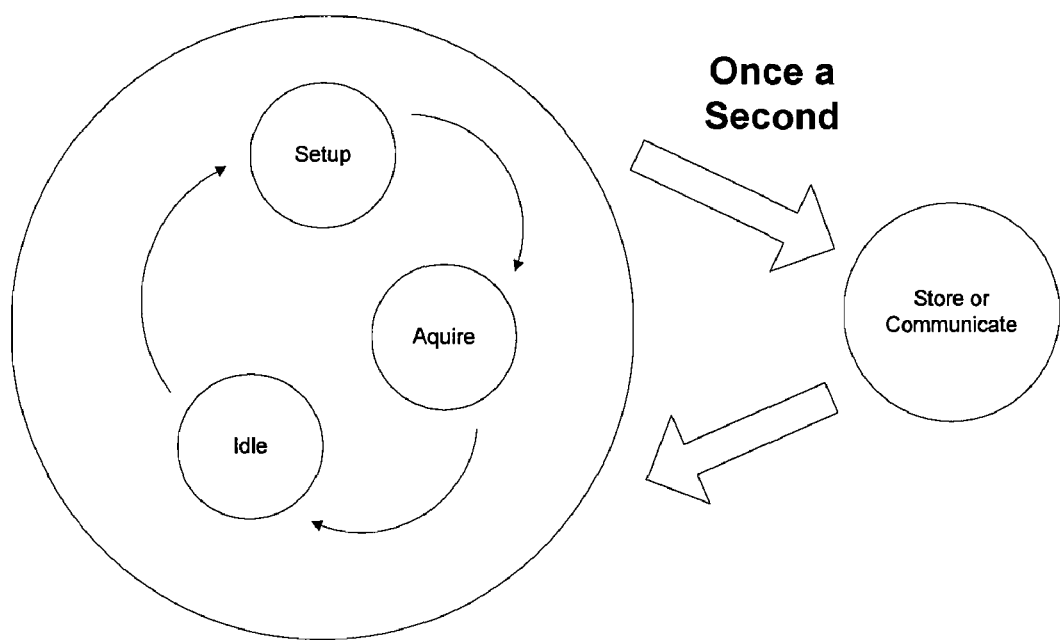
FIG. 3 illustrates an exemplary flow diagram of a continuous loop based on sample rate.

FIG. 3 provides a visual diagram of the operating states in a sensor as an aid in understanding the power computations and equations as applicable to the embodiments of this invention. For example, the sensor could operate in a loop of 3 states: Setup, Acquire, and Idle. In the Setup state sensor application and peripheral components are configured. For example, an analog to digital conversion is enabled for one or more input channels at a set sampling frequency. In the Acquire state, data is acquired (moved into memory). Typical sources for acquisition include peripherals with a digital interface, or an analog to digital converter. These sources could be integrated within a single IC, or one or more modules (printed circuit boards). In the Idle state, sensor elements are disabled and powered down to maximize runtime. FIG. 3 also shows a periodic Store or Communicate state. It is within this state that communication with the base-station occurs. The communication may be an input to the fault detector or an output that actuates a sensor indicator. Time spent in each state is required to be not equal, but may be so, and will depend on data rates and communication requirements.

Figure 4:
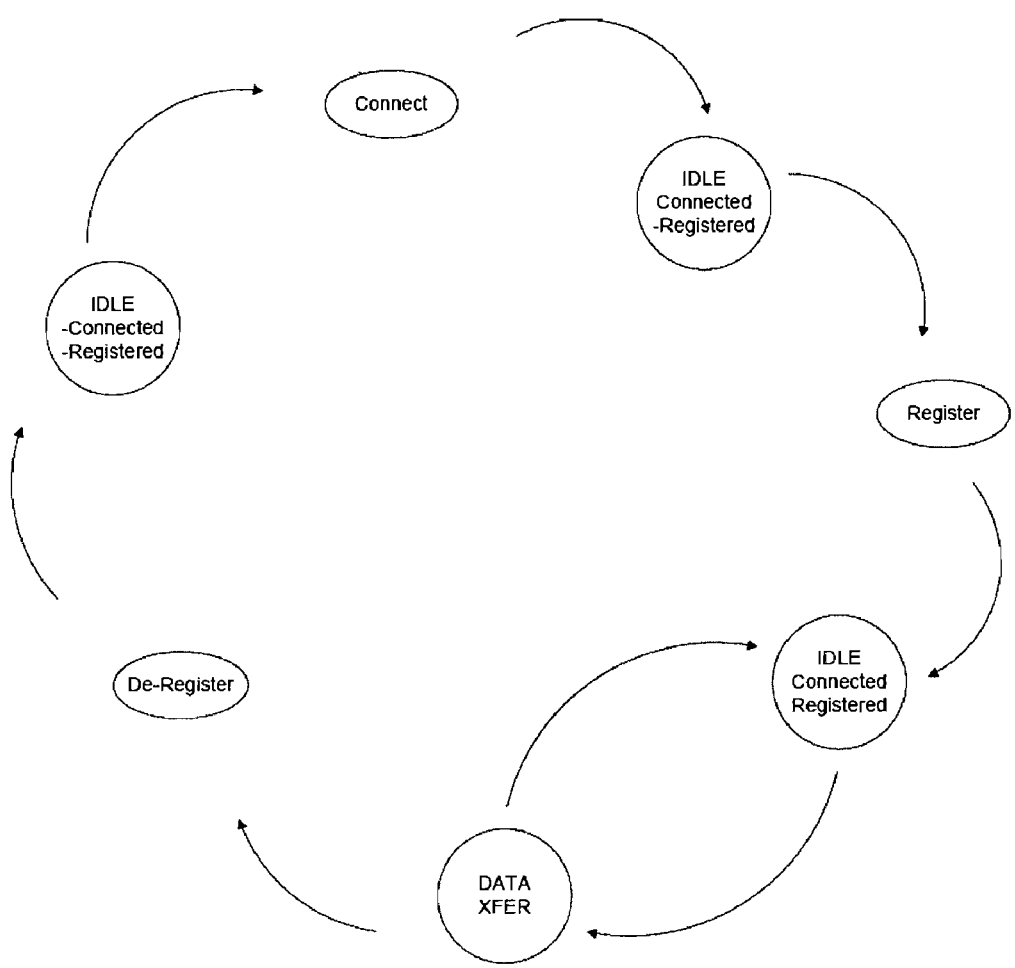
FIG. 4 illustrates an exemplary flow of connection, registration and data transfer for the sensor.

FIG. 4 shows a view of the states that comprise the communicate action that a sensor may perform once operational but not engaged in a data acquisition. From the "IDLE-Connected/-Registered" state—meaning that the device is neither connected nor registered with a base station—the sensor first initiates a connection with a base station. Upon connection, the sensor enters the next IDLE state, from which it will attempt to register itself with the base station; once registered, the sensor will begin transferring status and/or acquisition data to the base station. This transfer may involve multiple iterations of the transitions between "IDLE Connected/Registered" and "DATA XFER," as necessary to move all required information packets and to allow for interceding acquisitions. Upon completion of data transfer transaction, the sensor will notify the base station that its transfer is complete by sending a de-registration message; at this point the sensor will drop its connection to the base station as well.

Figure 5:
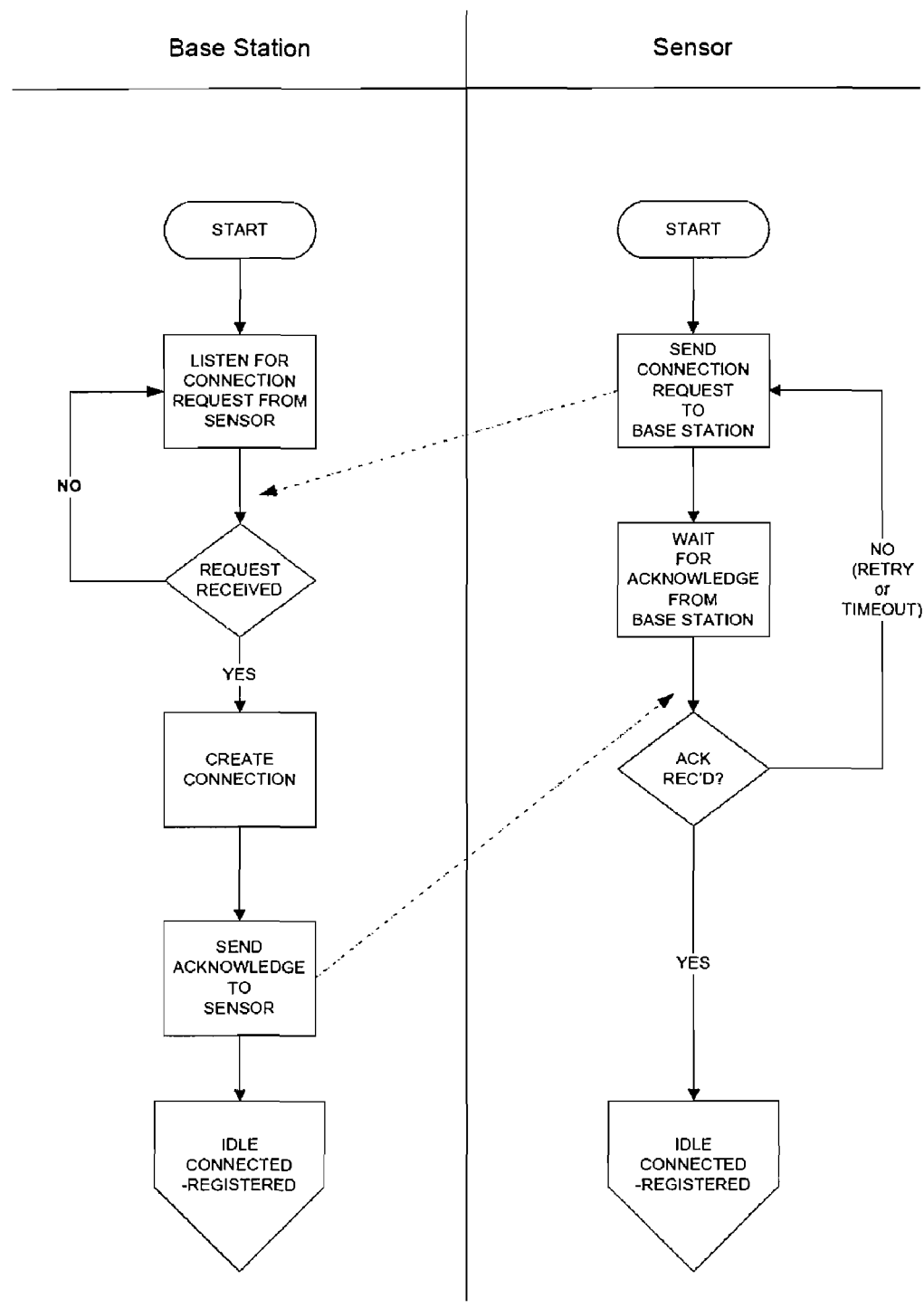
FIG. 5 illustrates an exemplary flow of data between the base station and sensor when neither are connected.

FIG. 5 breaks out the detail of the communications during the "IDLE-Connected/-Registered" state between the base station and the sensor. The sensor initiates a conversation by sending a request for a connection; the base station responds with an affirmative acknowledgement "ACK." An "ACK" formally establishes the connected state between the two devices, whereupon the sensor can then make the transition to the next state "IDLE Connected/-Registered."

Figure 6:
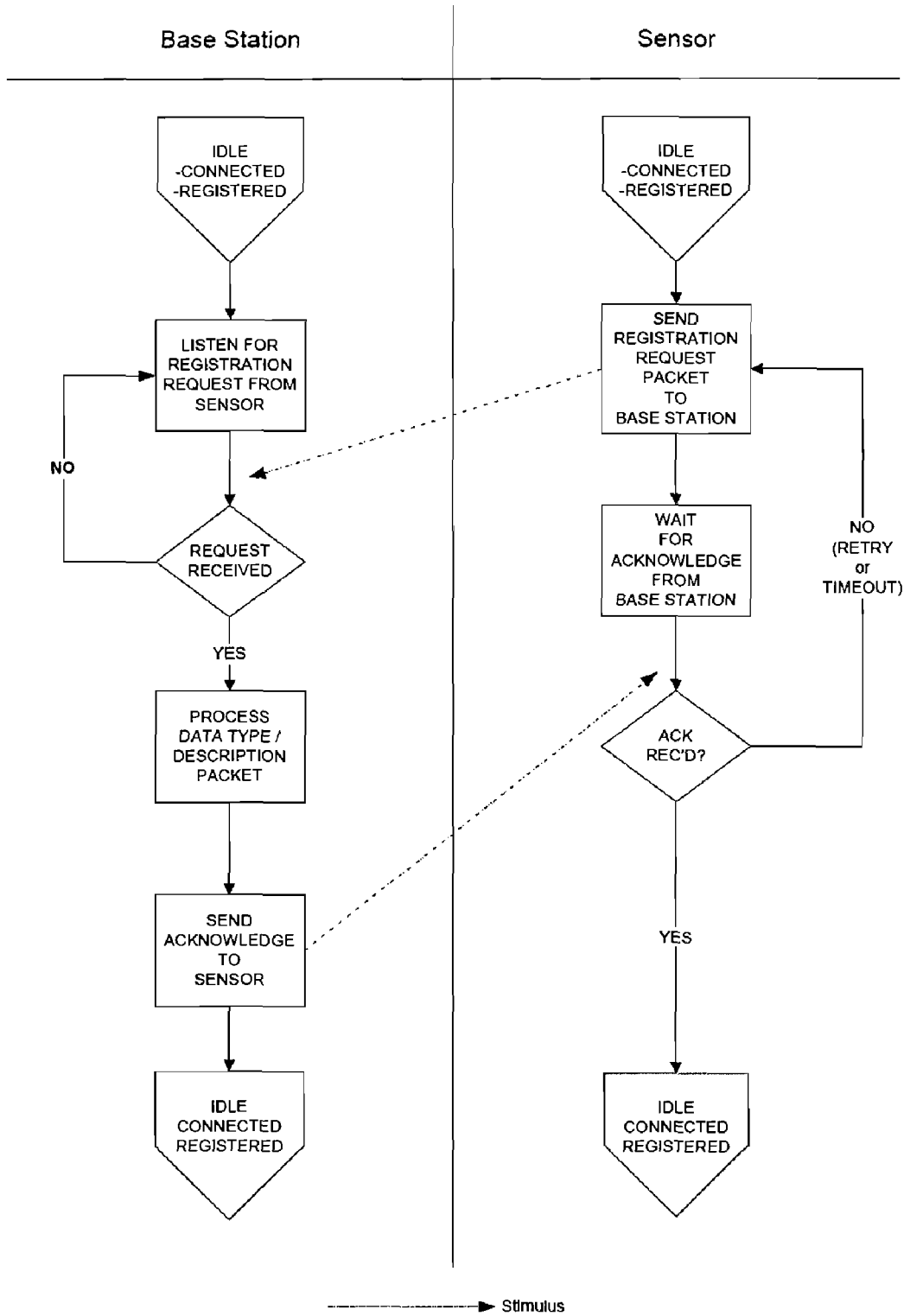
FIG. 6 illustrates an exemplary flow of data between the base station and sensor when the base station is connected and the sensor is not connected.

FIG. 6 shows detail of the communications involved in the registration process between the base station and the sensor in the "IDLE Connected/-Registered" state. Similar to the connection process, the base station awaits a registration packet from the sensor after the two devices establish a connection. Once this packet is received and processed, the base station replies with an "ACK." The devices are now prepared to enter a data transfer cycle.

Figure 7:
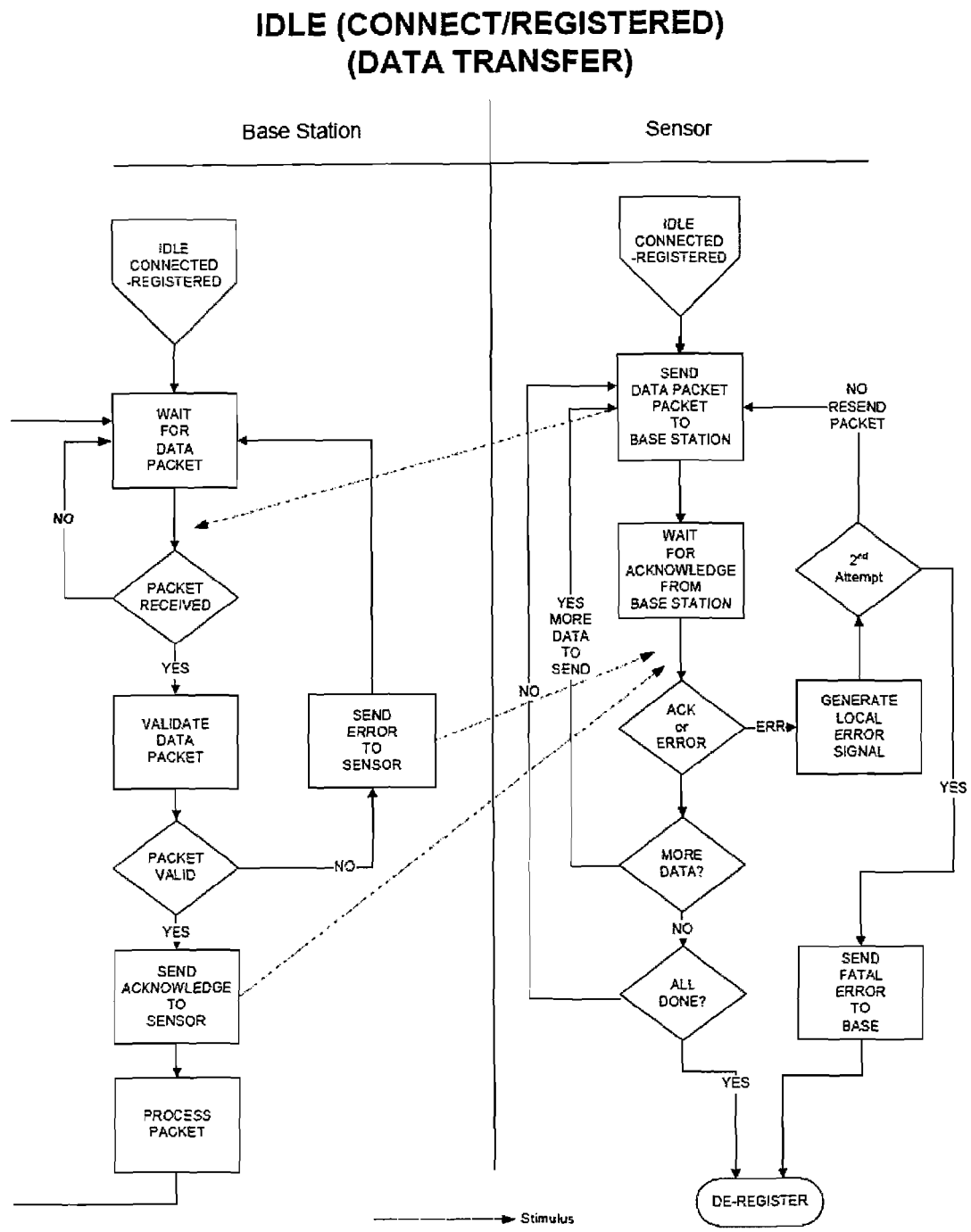
FIG. 7 illustrates an exemplary flow of data between the base station and sensor when both are connected and data transfer occurs.

FIG. 7 details the communications between the base station and the sensor once the sensor has connected and registered with the base station, and the two devices are in the data transfer process. An individual transfer is triggered by the sensor sending a data packet to the base station. The base station validates the data format and/or data values sent, then responds with either an "ACK" or an error message. Either response allows the sensor to respond with—in the case of an "ACK"—another data packet, or a de-registration packet if it has transferred all of its data. If the base station sends an error signal, then the sensor can either re-send the data packet based upon some recovery constraint—the figure shows a attempt counter, but another metric may be employed—or enter an error/alarm condition by notifying the base station, thereby de-registering and entering the "IDLE-Connected/-Registered" state.

The sensors could have several different configurations. One feature of the sensor configuration includes a coordinating base-station (also commonly called an aggregation device or sensor gateway) with the ability for user to invoke assistance in maintaining a sensor network; ability to communicate with sensors to determine status of consumables such as power and chemical agents and verify signal quality from affixed sensors that might "fall off" during activity; and physical interface to refresh depleted sensor resources.

Another feature of the sensor configuration includes one or more sensors with ability to communicate status to coordinating base-station (as described above) and ability to attract user attention such as a blinking indicator or audible alarm.

Yet another feature of the sensor configuration includes decision engine which is an application running on base-station or remotely via calls to the base station that can (1) access sensor status information; (2) activate sensor attention indicators based on a stored profile; and (3) be customized according to health care provider or patient preferences, capabilities of the sensor and the intended monitoring plan.

Some of the applications of the sensor network of the embodiments of the invention include detection of a fall by a person; determining medicine efficacy; detecting a change in behavioral or physiological behavior associated with management or new diagnosis of a disease; activity logging; detecting a change in behavior with no proven association with a disease state, e.g., performance training and personal journaling.

The method and apparatus of the embodiments of the invention have greater relevance and utility in a multi-sensor network with ability for base-station to communicate with the sensor nodes of the sensor network. Preferably, the sensor network is wireless. For example, a health monitoring sensor network could use a wireless communication method that is either standards based or proprietary to establish, exercise, and maintain communication.

In the embodiments of the invention, a sensor includes a transducer and the appropriate computation or electronics to encode or digitize the output of the transducer and satisfy wireless communication requirements. For example, in one embodiment the sensor could use a microcontroller to store and later transmit data, or stream data to a wireless transceiver. If the transducer has a digital output, then the transducer may be directly connected to the microcontroller. If the transducer has an analog output, a signal conditioning front end and analog to digital converter would be generally required.

Another feature of the sensor network of the embodiments of the invention is the base station, which generally has the following components: (1) method for user to invoke assistance—typically a button; (2) device for computation (microcontroller/CPU) to meet application requirements; (3) wireless communication hardware and communication software (network stack, firmware, etc.); (4) ability to determine sensor status and verify signal quality; and (5) interface to refresh depleted sensor resources. One example is a plug, connector, or power coupling system to re-charge sensor batteries. Another example concerns a sensor that has an element with operating lifetime limits such as an adhesive, or a chemical transducer that "expires" once activity—the base station would have an interface to assist with refreshing those resources.

There may be several base stations in a single physical location such as a home and sensor network could support mobility (roaming between multiple base-stations). The adaptation of multiple base-stations in a sensor network is merely choice of correctly using known computing components including software to meet functional requirements, and satisfactory human-factors and industrial engineering to meet user requirements.

In one embodiment, software could check several base-stations. For example, base stations could pass data to another system such as a service provider's backend to provide ability to check several base stations. The components of the software could include known methods and architectures for scalable computer systems could be used. Preferably, the base-station is not user configurable beyond the initial setup, which is analogous to other network appliances (home routers, wireless access points, cable modems, etc.).

In yet other embodiments, the system monitors a component of the at least one sensor that has a service life based on a number of activations, a duration of activation, or an operating condition. Preferably, the base-station has a capability to reset or replenish the component that limits service life to enable continuous operation of the health monitoring system. In accordance with these embodiments, the operational lifetime limit such as duration of activation which might be measured as a number of hours elapsed. An example would be that of an adhesive mount. Another example is the duration of time between transducer or sensor calibration. The number of activations would apply to a lifetime limit for number of uses. This may for example be due to chemical agents used in a sensor or based on finite and countable consumable supply used in the sensor, for example test strips in a medical monitor. The operating condition would describe datasheet values for temperature, shock, etc. that must be followed for the transducer to operate as designed.

Furthermore, the base-station could be adapted to be used by employing a single user button to initiate maintenance of a health monitoring system. For example, see FIG. 1 and the explanation on this figure, but in short this feature relates to the ability by which a single button could invoke the decision engine which would then compute the required output of the system.

In the embodiments of the invention, the base-station is adapted to send and receive data. The protocol for sending and receiving data are described below. For example, FIGS. 4-5 show how one might register a sensor with the base-station in, and FIG. 2 shows how the base-station might then check the operating status of the sensor and also check quality of sensor data. Furthermore, the sensors are adapted to communicate data to base-station, for example, the sensor can communicate and measure certain parameters (e.g., battery voltage).

Another feature of the sensor network of the embodiments of the invention is a fault-detection system that could be hardware, software or a combination thereof, but preferably is a software system. The fault detection system is for detecting a fault in the network system. Once a fault has been identified, the rectification would then generally happen at the base-station (for low-battery, or a depleted resource) or replacement of failed sensor device. The fault-detection system could detect when thresholds are exceeded (time, or a measured parameter) and/or detect when data is out of range of normal range that could be based on methods of data analysis and inference such as rules/decision tree, statistical methods, or physical modeling.

Another function of the sensor network of the embodiments of the invention is to detect sensors that are at the end of operational life, failed transducers or other fragile components, and failed placement of sensors.

Preferably, the fault-detection system is adapted to analyze data from the sensor and determine an operating state of the sensor, i.e., whether the sensor is operating normally or abnormally. The fault-detection system could be located in the base station or on a remote computing resource. The remote computing resource would generally not be at the home; it would be elsewhere in the world network, e.g., hosted by a service provider. In some embodiments of the invention, there could be multiple remote computing resources that communicate with the sensor network. However, generally, the remote computing resources are not configurable by the user, but can be configured by the service provider who maintains the remote computing resource.

Yet another feature of the sensor networks of the embodiments of the invention relates to a decision engine, which could be more than one per sensor network, but preferably there is one decision engine per sensor network. The decision engine causes output action (actuation) based on one or more system inputs. The decision engine could be adapted to activate a sensor attention indicator, e.g., a visual indicator such as display screen, lamps, LEDs; an audio indicator such as speaker output, buzzer, or chirper; or a tactile indicator preferably having a vibration.

In one embodiment of the invention, the base station bi-directionally communicates with the at least one sensor. In yet another embodiment, the sensor system is adapted to notify a detected fault on the at least one sensor by notifying an user and/or a system administrator or management professional. The notification can be real-time or scheduled depending on user or administrator preferences.

In one embodiment of the invention, the base station hosts a secure, remotely-configurable bridge to the sensor network. This could be done by a standard protocol, typically IP (internet protocol), and associated extensions for secure sessions. Other methods of connectivity suitable for bridging to the sensor network include telephone-modem (POTS), cellular or satellite data connections, and WLAN or long-range wireless communication.

Preferably, the sensor system has a sensor that captures data from an accelerometer, an optical motion detector, or an object motion detector such as a vibration or tilt transducer.

In one embodiment the sensor system has a sensor that captures data from a MEMs accelerometer.

In another embodiment the sensor system has a sensor that captures data from a PIR (passive infra-red) motion detector.

In one embodiment of the invention, upon initialization of communication between the base station and the at least one sensor, the system is adapted to start a registration process.

Furthermore, in the embodiments of the invention, at least one sensor could be adapted to send header information to the base station including at least one of the following: information about data-type for scalar quantity measure by the device, valid range, units for the scalar, frequency of delivery, and a descriptive character string; and the base station could be adapted to reply with an acknowledgement message. Preferably, upon receipt of an error signal from the base station, the at least one sensor actuates a detectable alarm. Preferably, the decision engine includes a user stored profile based on data supplied by a healthcare provider or a patient to allow customization of the decision engine to meet capabilities and requirements of patients (users). For example, a 50 year old with mild heart disease would have different capabilities then a 90 year old with dementia from Alzheimer's.

In yet another aspect of the invention, and upon initialization of communication between the base station and the at least one sensor, a registration process occurs (see FIG. 6).

In one aspect of the invention, the registration process comprises the at least one sensor sending header information to the base station including at one of the following: information about data-type for scalar quantity measure by the device, valid range, units for the scalar, frequency of delivery, and a descriptive character string; and the base station replies with an acknowledgement message (see FIG. 6).

In another aspect of the invention, and upon receipt of an error signal from the base station, the at least one sensor actuates a user detectable alarm (see FIG. 7).

In still another aspect of the invention, the decision engine is customizable and includes a user stored profile based on data supplied by a healthcare provider or patient sensing requirements.

Exemplary elements of the invention are:
A) Coordinating base-station with:
  1) Method for user to invoke assistance in maintaining a sensor network.
  2) Ability to communicate with sensors to determine status of consumables such as power and chemical agents and verify signal quality from affixed sensors that might "fall off" during activity.
  3) Physical interface to refresh depleted sensor resources.
B) Wearable sensors with:
  1) Ability to communicate status to coordinating base-station (as described above).
  2) Ability to attract user attention such as a blinking indicator or audible alarm.
C) Decision engine that can:
  1) Access sensor status information.
  2) Activate sensor attention indicators based on a stored profile.
  3) Be customized according to health care provider or patient preferences, capabilities of the sensor and the intended monitoring plan In another embodiment of the invention, there is a method to provide assistance in the maintenance of a health monitoring system by automating detection of faulty or failed sensors using real-time fault-checking on a dynamically registered sensor data stream. The monitoring system and sensor network can provide a one-touch system to notify users when a sensor requires attention. The user need not have prior knowledge of the operational characteristics, installation method, or configuration of sensors in the network to unambiguously detect a fault.

Additional exemplary elements are:
  A base station that has the ability to conduct bi-directional communications with sensors in the health monitoring system. Data from each sensor is presented to a fault-detection service for checking and the results are used to notify users of faults on specific sensors at an opportune time. The base station hosts a secure, remotely-configurable bridge to the local health monitoring network.
  A number of portable sensors that can, upon initialization, notify the base station of the nature of their data transmissions, and accept a message from the base station that triggers either a visible or audible trouble indicator.
  A fault-detection service that can select and apply data-checking based on a library of methods associated with specific registered data types and available computational resources.

The embodiments of the invention address the problem(s) of:
  Deploying and maintaining a long-term multi-sensor system offering new diagnostic and intervention options for a wide range of conditions. The adoption of these systems requires new methods of automated assistance because in many cases the target population has limited knowledge of technology, physical or cognitive impairment, and limited patience for sensing systems that further marginalize their quality of life.

The diminutive form-factor of on-body sensors in multi-sensor systems requires regular intervention to maintain effectiveness in long-term monitoring scenarios. In a multi-sensor system the complexity of maintenance is multiplied and will require new methods of user assistance and deployment.

Self-powered sensors located around users (environmental sensors) offer advantages for mass-casualty events and other temporary deployments. Minimizing maintenance overhead while ensuring reliable operation is a strong product advantage.

The invention provides a method of assisted maintenance based on system components that are well understood.

The embodiments of the invention simplify the maintenance of a health monitoring sensor system by autonomously validating data from a dynamic group of homogeneous or heterogeneous sensors, and provides a facile method that requires no user training for locating a faulty sensor.

Examples of fault conditions include:
  1) Sensors that are dislodged from their mounting point.
  2) Sensors with consumable properties or limited operating lifetime.
  3) Sensors that become inoperable due to power transients or corrupted memory.
  4) Sensors that become inoperable due to tampering by visitors, pets or pests.

For long term sensing, the method and mechanism described will limit the burden on the patient according to a customizable profile that guides a decision engine. The system will assist the user in preventative maintenance of the sensor network at the user's request. This method is easily adapted into the patient's daily routine.

The direct result will be longer periods of multi-sensor data capture on a wider range of individuals.

The consumable aspects of sensor design can be implemented with less design margin. Relaxing design margins will result in smaller, simpler and less expensive sensor systems providing competitive advantage over multi-sensor systems that do not use the techniques described.

The system ensures robust data collection in a dynamic sensing environment by allowing technically naïve users to isolate faults to a specific sensor.

The system relieves sensor devices with modest processing resources of the burden of self-diagnosis.

The system is extensible and supports remote management and customization.

EXAMPLES

An exemplary embodiment of one detailed application relates to the case of a multi-limb motion capture system for physical rehabilitation, such as stroke recovery. Referring to the embodiment in FIG. 1, ten sensors with 7-day battery life and recording capability are placed on the body (one for each limb segment and two on the torso). Data from accelerometers in the sensor will be used to form a detailed model of body kinetics to guide treatment. The data set created by monitoring the sensors will be especially valuable since the user will be performing natural activities. However, maintaining ten sensors, for example for 2-3 weeks, is burdensome—the sensors look the same and are easily confused. Without assistance the user will be forced to charge all ten blindly every few nights to ensure battery life. The charging apparatus will be bulky and intimidating.

To assist the user and dramatically improve the usability of the sensor system, the proposed methods are employed using at least the following decision engine rules:

Ensure sensors have safety margin in remaining battery life; and

Indicate best sensor for charging when prompted by user for maintenance assistance.

The patient can now maintain the sensing system, for example, based on a simple set of instructions:
1) Every night when you remove the sensors before sleep, go to the small charging base-station and press the button.
2) Place the sensor with an indicator illuminated in the base-station for maintenance (in this case data transfer and battery charging).

Over, for example, the three week period of monitoring as described above, the sensors are rotated through the base-station and the simple maintenance procedure becomes second nature much like charging a cellular phone.

Referring to the embodiment in FIGS. 5 and 6, the base station acts as server to sensor clients, which perform a two-step registration process during initialization of communications. The client sends header information to the base station including information including data-type for scalar quantity measured by the device, valid range, units for the scalar, frequency of delivery, and a descriptive character string. The base station replies with an acknowledgement message.

The base station calls a fault detection service to check sensor data for proper operation. A simple example would be to perform temporal and scalar bounds-checking for each sensor's data stream with aberrant values measured against the device's recent historical trend. A more complex system may use modeling and machine learning techniques to qualify the sensed data using additional data sources (time of day, season, etc.)

Sensors can be quite different or have subtle failure modes making manual checking tedious for humans, but the process is easily automated using the method herein described.

The fault detection service can be hosted in the base station or on a remote computing resource depending on the processing requirements.

The sensor acts as client to base station server, but listens for spurious messages from server. After registration, sensor minimizes communications to data transmission. Upon receipt of an error signal from base station, the sensor actuates a human-detectable alarm, for example, a low power blinking LED. A one-touch-for-maintenance system may log a sensor fault but wait for a user button-press to signal a fault.

Referring to the tables below, one method of sensor operating life calculation is to use average current during a repeated sampling window according to the following equation:

$$IAvg = (tStore \times IStore) + (tComm \times IComm) + [(tWindow - Store - tComm) \times IAcq)] \quad (1)$$

MEMs accelerometers are useful sensors. The following table was populated based on the operating specifications of an ultra-low power CPU acquiring 16 bit samples for X-Y-Z data using DMA and power saving modes (subject to timing constraints).

| Sampling Rate (Hz), use | IAcq (mA) | Bits per second |
|---|---|---|
| 10, activity segmentation | .090 | 480 |
| 50, gesture recognition | .44 | 2400 |
| 100, clinical grade measurement | .90 | 4800 |

Using conservative values of 20 mA for IStore (better then state-of-the-art for reliable standards based wireless communication or flash media) and an aggressive transfer rate of 0.5 Mbps the following table can be computed using the previous table and equation 1. The table shows best case sensor operating life for 4 common form factors:

| Sampling Rate (Hz) | tStore(s) | IAvg (mA) | Button, 100 mAh | Key-Fob, 250 mAh | Pager, 500 mAh | Phone, 1000 mAh |
|---|---|---|---|---|---|---|
| 10 | .001 | .12 | 35 days | 87 days | 174 days | 350 days |
| 50 | .005 | .30 | 14 days | 35 days | 69 days | 140 days |
| 100 | .01 | .59 | 7 days | 18 days | 35 days | 70 days |

Adding extra degrees of sensing will result in even shorter operating life—e.g. ½ as long when collecting all 6-axis of motion.

Returning to the case of a clinical grade gait and motion capture system using ten sensors, each sensor would require a 500 mAh battery for one month of data capture. The proposed system for assisted maintenance would allow the user to continuously rotate through considerably smaller sensors without guidance from a caregiver. For example, a key-fob sized device would provide margin and a single sensor could be recharged every night. If the sensor system requires wireless communication, real-world data transfer rates can be up to 100× worse then the numbers above due to packet loss Alternatively, in a preferred embodiment with reference to the table above and FIG. 7, sensor operation is repetitive and can be expressed as a repetitive loop consisting of states for data acquisition, data storage, data communication, and sensor idle. Over time, the average power consumed by the sensor will be equal to a sum of terms for power in each state weighted by time spent in each state. In the likely worst case, current draw for each state can be determined from a static value from device datasheets.

For battery powered devices, power is approximated by=Current draw on a battery with a manufacturer's mAh rating. Therefore power in a state is approximated by current, not current*voltage.

From these assertions, an equation for average current in a repetitive loop is derived:

Average Current/Many Identical Loops~=Current/Loop

Average Current=[Time spent storing*Current while storing]+[Time spent communicating*Current while communicating]+[Time spent in setup to acquiring data*Current in setup to acquiring data]+[Time spent acquiring data*Current while acquiring data]+[Time spent Idle*Current while Idle]

$$IAvg=[tStore*IStore]+[tComm*IComm]+[tSetup*ISetup]+[tAcq*IAcq]+[tIdle*IIdle] \quad (1)$$

It can be observed that:

$$tLoop=tStore+tComm+tSetup+tAcq+tIdle \quad (2)$$

To simplify notation, an average current for Setup, Acquire and Idle states could be calculated with 100 Hz Sampling:

The acquisition process uses data from datasheets for timing requirements and current consumption (e.g., 1.3 mA=ICPUinDMA+IADC+IAccelerometer) and involves the following states:
1) Idle;
2) Enable on the accelerometer so that power can stabilize (setup to acquiring data); and
3) Enable the ADC and sample X/Y/Z data points.

The number in the time row is the sample period, the number below is the calculated average current.

Bits per second can be calculated easily:

Samples per second*bits per sample*channels sampled=bits per second.

For 10Hz:

10*16*3=480 bps

For 50 Hz, the value is 2400 bps
For 100 Hz the value is 4800 bps
From this we get the completed first and second tables above.
So:

$$IAvg=[tStore*IStore]+[0*IComm]+[tSampling*ISampling] \quad (2)$$

See Continuous Loop based on Sample Rate (FIG. 7).

tStore=Bits per second/data transfer rate.

tSampling and ISample are calculated based on the sample rate chart above.

The second table above is based on plugging results to equation (1) using Istore=20 ma and a data transfer rate of 0.5 Mbps. Also tComm is set to zero since Istore is less then IComm in most cases.

For 10 Hz and communication every second:

Iavg=((0.001 s)*20 mA)+(1 s−0.001 s)*0.091 mA=0.11 mA

For 50 Hz and communication every second:

Iavg=((0.005 s)*20 mA)+(1 s−0.005 s)*0.44 mA=0.53 mA

For 100 Hz and communication every second:

Iavg=((0.010 s)*20 mA)+(1 s−0.010 s)*0.88 mA=1.1 mA

Finally, battery life is calculated using the formula:

Operating life (hrs)=[(Battery capacity (mAh)/Iavg)]

Operating life days=Operating life hrs/24

For 10 Hz:

100 mAh/0.11 ma=909 hrs=38 days 250 mAh/0.11 ma=2272 hrs=95 days 500 mAh 0.11 ma=4545 hrs=189 days 1000 mAh/0.11 ma=9091 hrs=379 days For 50 Hz:

100 mAh=8 days 250 mAh=20 days 500 mAh=39. days 1000 mAh=79 days

For 100 Hz:

100 mAh=4 days 250 mAh=10 days 500 mAh=19 days 1000 mAh=38 days

Additional advantages of this invention will become readily apparent to those skilled in this art from the following detailed description, wherein only the preferred embodiments of this invention is shown and described, simply by way of illustration of the best mode contemplated for carrying out this invention. As will be realized, this invention is capable of other and different embodiments, and its details are capable of modifications in various obvious respects, all without departing from this invention. Accordingly, the drawings and description are to be regarded as illustrative in nature and not as restrictive. While embodiments of the invention have been particularly shown and described with references to embodiments thereof, it will be understood by those skilled in the art that various changes in form and details may be made therein without departing from the scope of embodiments of the invention encompassed by the appended claims.

This application discloses several numerical ranges in the text and figures. The numerical ranges disclosed support any range or value within the disclosed numerical ranges even though a precise range limitation is not stated verbatim in the specification because this invention can be practiced throughout the disclosed numerical ranges. In the claims, the terms "a" and "an" mean one or more. Finally, the entire disclosure of the patents and publications referred in this application are hereby incorporated herein by reference.

The invention claimed is:

1. A system, comprising:
a base station adapted to wirelessly receive data from a first sensor, the base station comprising:
a fault detection unit adapted to detect a faulty operating state of the first sensor based on whether a value of the data received from the first sensor is within a predefined sensor data value range stored on the base station, based on a frequency of delivery of the sensor data on a time of day the sensor data was received from the first sensor, a season in which the sensor data was received from the first sensor, based on estimating remaining sensor operating life or based on any combination thereof, and
a decision engine unit adapted to cause the base station to wirelessly transmit an attention indicator activation command to the first sensor to activate an attention indicator on the first sensor based on the detected faulty operating state of the first sensor.

2. The system of claim 1, wherein the fault detection unit is adapted to determine the operating state of the first sensor based on a frequency of delivery of the sensor data.

3. The system of claim 1, wherein the fault detection unit is adapted to estimate the remaining sensor operating life based on a sensor current consumption rate value stored on the base station and to determine the operating state of the first sensor based on the estimated remaining sensor operating life.

4. The system of claim 1, wherein the base station is adapted to host a secure, remotely-configurable bridge to the sensor network.

5. The system of claim 1, wherein the base station further comprises a user input configured to trigger the fault detection unit to determine whether the first sensor needs maintenance.

6. The system of claim 1, wherein the first sensor comprises an accelerometer, a motion detector, or object motion detector.

7. The system of claim 1, wherein upon initialization of communication between the base station and the first sensor, the system is adapted to start a registration process.

8. The system of claim 1, wherein:
the first sensor is adapted to send header information to the base station including at least one of the following: information about data-type for scalar quantity(s) measured by the device, valid range, units for the scalar, frequency of delivery, and a descriptive character string; and the base station is adapted to reply with an acknowledgement message.

9. The system of claim 1, wherein the decision engine unit includes a user stored profile based on data supplied by a healthcare provider or a patient.

10. A method, comprising:
receiving wirelessly, at a base station, data from a first sensor;
detecting, at the base station, a faulty operating state of the first sensor based on whether a value of the data received from the first sensor is within a predefined sensor data value range stored on the base station, based on a frequency of delivery of the sensor data based on a time of day the sensor data was received from the first sensor, a season in which the sensor data was received from the first sensor, based on estimating remaining sensor operating life station, or based on any combination thereof; and
transmitting wirelessly, from the base station to the first sensor to activate an attention indicator on the first sensor, an attention indicator activation command based on the detected faulty operating state of the first sensor.

11. The method of claim 10, wherein the fault detection unit is adapted to determine the operating state of the first sensor based on a frequency of delivery of the sensor data.

12. The method of claim 10, wherein estimating the remaining sensor operating life is based on a sensor current consumption rate value stored on the base station, and wherein determining the operating state of the first sensor is based on the estimated remaining sensor operating life.

13. The method of claim 10, wherein the base station is adapted to host a secure, remotely-configurable bridge to the sensor network.

14. The method of claim 10, wherein the base station further comprises a user input configured to trigger the fault detection unit to determine whether the first sensor needs maintenance.

15. The method of claim 10, wherein the first sensor comprises an accelerometer, a motion detector, or object motion detector.

16. The method of claim 10, wherein upon initialization of communication between the base station and the first sensor, the system is adapted to start a registration process.

17. The method of claim 16, wherein the registration process comprises:
sending, via the first sensor, header information to the base station including at least one of the following: information about data-type for scalar quantity measure by the device, valid range, units for the scalar, frequency of delivery, and a descriptive character string; and replying, via the base station, with an acknowledgement message.

18. The method of claim 10, wherein the base station comprises a power charging interface configured to provide power to the first sensor.

19. The method of claim 10, wherein the decision engine unit includes a stored user profile based on data supplied by a healthcare provider or a patient.

20. The system of claim 1, wherein the base station is adapted to monitor a component of the first sensor that has a service life based on a number of activations, a duration of activation, or an operating condition.

21. The system of claim 5, wherein the user input is configured to trigger the fault detection unit to determine whether a battery of the first sensor needs to be charged.

22. The system of claim 20, wherein the base-station has a capability to reset or replenish the component that limits service life to enable continuous operation of the health monitoring system.

23. A system, comprising:
a sensor network comprising a first sensor;
a base station adapted to wirelessly receive data from the first sensor to activate an attention indicator on the first sensor, the base station comprising:
a fault detection unit adapted to detect a faulty operating state of the first sensor based on whether a value of the data received from the first sensor is within a predefined sensor data value range stored on the base station, based on a frequency of delivery of the sensor data based on a time of day the sensor data was received from the first sensor, a season in which the sensor data was received from the first sensor, based on a sensor current consumption rate value stored on the base station, or based on any combination thereof, and
a decision engine unit adapted to cause the base station to transmit an attention indicator activation command to the first sensor based on the detected faulty operating state of the first sensor.

24. A method, comprising:
transmitting, from a first sensor of a sensor network, data to a base station;
receiving wirelessly, at a, base station, data from the first sensor;
detecting, at the base station, a faulty operating state of the first sensor based on whether a value of the data received from the first sensor is within a predefined sensor data value range stored on the base station, based on a frequency of delivery of the sensor data based on a time of day the sensor data was received from the first sensor, a season in which the sensor data was received from the first sensor, based on a sensor current consumption rate value stored on the base station, or based on any combination thereof; and
transmitting from the base station to the first sensor to activate an attention indicator on the first sensor, an attention indicator activation command based on the detected faulty operating state of the first sensor.

25. The system of claim 22, wherein the capability to rest or replenish the component that limits service life comprises a power charging interface configured to provide power to the first sensor.

26. The system of claim 20 wherein the component of the first sensor being monitored comprises a battery.

* * * * *